US009983131B2

(12) United States Patent
Compton (10) Patent No.: US 9,983,131 B2
(45) Date of Patent: May 29, 2018

(54) ATOMIC SOURCE WITH HEATER ON THERMAL ISOLATION DIE

(71) Applicant: Honeywell International Inc., Morristown, NJ (US)

(72) Inventor: Robert Compton, Plymouth, MN (US)

(73) Assignee: Honeywell International Inc., Morris Plains, NJ (US)

( * ) Notice: Subject to any disclaimer, the term of this patent is extended or adjusted under 35 U.S.C. 154(b) by 1077 days.

(21) Appl. No.: 14/249,012

(22) Filed: Apr. 9, 2014

(65) Prior Publication Data

US 2015/0226669 A1    Aug. 13, 2015

Related U.S. Application Data

(60) Provisional application No. 61/939,090, filed on Feb. 12, 2014.

(51) Int. Cl.
*G01N 21/64* (2006.01)
*G04F 5/14* (2006.01)
*H03B 17/00* (2006.01)
*G01N 1/28* (2006.01)
(Continued)

(52) U.S. Cl.
CPC .......... *G01N 21/6404* (2013.01); *G01K 7/00* (2013.01); *G01K 13/02* (2013.01); *G01N 1/28* (2013.01); *G04F 5/145* (2013.01); *H03B 17/00* (2013.01)

(58) Field of Classification Search
CPC ............... G01N 21/6404; G01P 15/038; G01P 15/0802; G04F 5/14; G04F 5/145; H03B 17/00; H03L 7/26

USPC .............. 73/514.01, 514.03, 514.05–514.09, 73/514.11, 514.13; 331/3, 94.1
See application file for complete search history.

(56) References Cited

U.S. PATENT DOCUMENTS 3,519,949 A    7/1970  Malnar et al.
3,577,069 A    5/1971  Malnar
(Continued)

FOREIGN PATENT DOCUMENTS

EP    2535779    12/2012
EP    2650737    10/2013

OTHER PUBLICATIONS

European Patent Office, "Partial European Search Report from EP Application No. 15152956.7", "from Foreign Counterpart of U.S. Appl. No. 14/249,012", dated Jun. 2, 2016, pp. 1-6, Published in: EP.

(Continued)

*Primary Examiner* — Levi Gannon
(74) *Attorney, Agent, or Firm* — Fogg & Powers LLC (57) ABSTRACT

In one embodiment, a chip scale atomic sensor is provided. The chip scale atomic sensor includes a body that defines at least one sensing chamber. The body includes a thermal isolation die mounted to the body. The thermal isolation die is disposed in a location that communicates with the at least one sensing chamber. The thermal isolation die includes a substrate defining a frame portion and an isolated portion and a plurality of tethers mechanically coupling the isolated portion of the substrate to the frame portion. The thermal isolation die also includes an atomic source mounted on the isolated portion of the substrate, and a heating element mounted on the isolated portion and configured to heat the atomic source.

27 Claims, 4 Drawing Sheets

(51) Int. Cl.
*G01K 13/02* (2006.01)
*G01K 7/00* (2006.01)

(56) References Cited

U.S. PATENT DOCUMENTS

| | | | | |
|---|---|---|---|---|
| 4,434,406 | A * | 2/1984 | Fowks | H03L 7/26 |
| | | | | 313/550 |
| 6,570,459 | B1 * | 5/2003 | Nathanson | G04F 5/14 |
| | | | | 331/94.1 |
| 2006/0257296 | A1 | 11/2006 | Lipp | |
| 2007/0025187 | A1 | 2/2007 | Agesawa et al. | |
| 2007/0266784 | A1 * | 11/2007 | Lust | G01C 19/62 |
| | | | | 73/504.05 |
| 2010/0026394 | A1 * | 2/2010 | Davis | H03L 7/26 |
| | | | | 331/3 |
| 2011/0031969 | A1 | 2/2011 | Kitching et al. | |
| 2011/0075692 | A1 * | 3/2011 | Moench | H03L 7/26 |
| | | | | 372/32 |
| 2013/0175455 | A1 * | 7/2013 | Cheng | G01J 3/4406 |
| | | | | 250/458.1 |

OTHER PUBLICATIONS

European Patent Office, "European Search Report for EP Application No. 15152956.7 dated Oct. 18, 2016", "from Foreign Counterpart of U.S. Appl. No. 14/249,012", dated Oct. 18, 2016, pp. 1-10, Published in: EP.

* cited by examiner

ATOMIC SOURCE WITH HEATER ON THERMAL ISOLATION DIE

CROSS-REFERENCE TO RELATED APPLICATIONS

This application claims the benefit of priority to U.S. Provisional Application No. 61/939,090, filed on Feb. 12, 2014, the disclosure of which is hereby incorporated herein by reference.

BACKGROUND

Atom based sensors including atomic clocks and atomic inertial sensors use an alkali metal source that releases alkali metal atoms to form an alkali vapor in a sensing chamber. One type of atom based sensor is a laser cooled sensor. Laser cooled atom based sensors use one or more laser beams directed at the alkali vapor to cool an atomic sample of alkali atoms in the alkali vapor.

Rubidium (Rb) and Cesium (Cs), which are commonly used alkali metals in atom based sensors, have melting points at or below 40 degrees Celsius, and exponentially increasing vapor pressures. Using such an alkali metal in many atom based sensor applications can result in an undesirably high vapor pressure in the sensing chamber. This high vapor pressure results in a large background vapor that collides with the laser cooled atoms and limits the lifetime of the atomic sample.

In order to reduce the background vapor pressure the alkali metal source can be composed of an alkali metal with at least one other element to form an alloy or compound that has a lower vapor pressure at the operating temperature than the alkali metal by itself. The source material can also be composed of a graphite intercalation compound that includes an alkali metal.

SUMMARY

In one embodiment, a chip scale atomic sensor is provided. The chip scale atomic sensor includes a body that defines at least one sensing chamber. The body includes a thermal isolation die mounted to the body. The thermal isolation die is disposed in a location that communicates with the at least one sensing chamber. The thermal isolation die includes a substrate defining a frame portion and an isolated portion and a plurality of tethers mechanically coupling the isolated portion of the substrate to the frame portion. The thermal isolation die also includes an atomic source mounted on the isolated portion of the substrate, and a heating element mounted on the isolated portion and configured to heat the atomic source.

DRAWINGS

Understanding that the drawings depict only exemplary embodiments and are not therefore to be considered limiting in scope, the exemplary embodiments will be described with additional specificity and detail through the use of the accompanying drawings, in which.

In accordance with common practice, the various described features are not drawn to scale but are drawn to emphasize specific features relevant to the exemplary embodiments.

DETAILED DESCRIPTION

Example binary alloys suitable for an atomic source include Rubidium-Indium (Rb—In), Rubidium-Lead (Rb—Pb), and Rubidium-Gallium (Rb—Ga). The melting temperatures for alloys with a small amount (around 10 percent) of (solute) metal in 90 percent alkali metal (solvent) are well above 100 degrees C. Further, the vapor pressures of the solute atoms are very low compared to the vapor pressure of the alkali solvent. This can enable atom based sensors using the composite atomic source to operate at elevated temperatures (around 100 degrees C.) with reduced vapor pressure as compared to elemental atomic sources. The ratio of solute to solvent can be selected to achieve the desired vapor pressure curve.

Atomic sources provided by graphite intercalation compounds can be comprised of mono or multi-atomic layer sheets of graphite separated by atomic monolayers of alkali metal. The ratio of carbon to alkali layers in the graphite intercalation compound can be selected to achieve the desired vapor pressure curve.

In either a binary alloy or graphite intercalation compound example, the composition of the atomic source can be selected to have a vapor pressure that is lower than desired at the highest desired operating temperature for the sensor. Then, the atomic source can be heated in a controlled manner to increase and maintain the desired vapor pressure in the sensing chamber. In an example, such an atomic source can be disposed on a thermal isolation die which allows low power temperature control of the atomic source. Advantageously, such a binary alloy or graphite intercalation compound can also act in a reversible manner to re-absorb excess alkali vapor from the sensing chamber.

Figure 1:
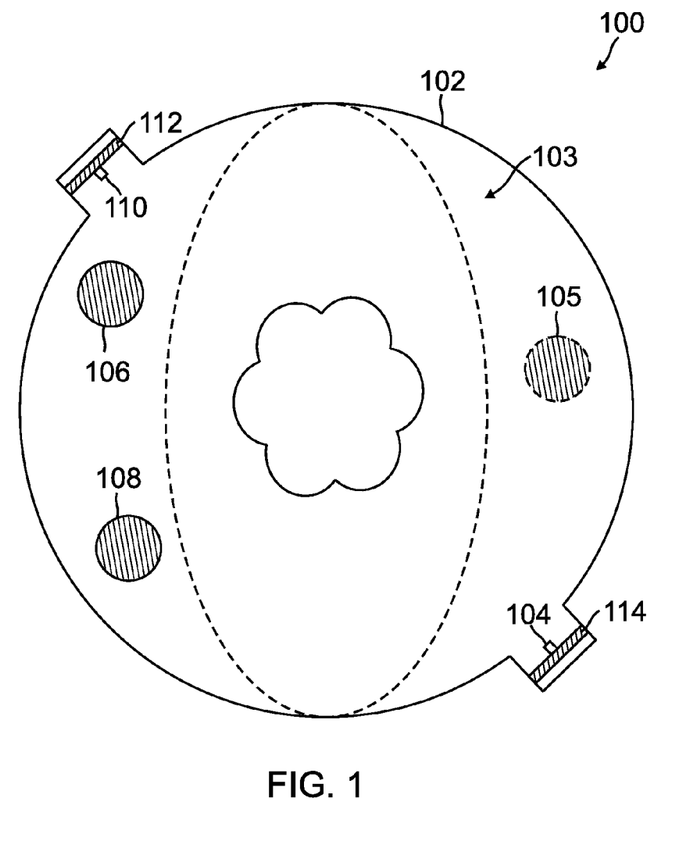
FIG. 1 is a plan view of an example physics package for a chip-scale atomic based sensor having an atomic source and heating element disposed on a thermal isolation die.

FIG. 1 is a plan view of an example physics package 100 for a chip-scale atomic based sensor. In an example, the physics package 100 is for an atomic clock. In another example, the physics package 100 is for an atomic inertial sensor. The physics package 100 includes a body 102 which defines a sensing chamber 103. The body 102 is a structural member and can be composed of any suitable material such as a glass or ceramic. In the example shown in FIG. 1, the body 102 is spherical, however, the body 102 can have any suitable geometry.

An alkali vapor is maintained within the sensing chamber 103. In an example, the alkali vapor is composed of Rubidium (Rb) atoms or Cesium (Cs) atoms. One or more lasers 104, 105, 106 are configured to emit light into the sensing chamber 103 in order to cool atoms in the alkali vapor, sense a state of the atoms, and/or sense a density of the alkali vapor. The one or more lasers 104, 105, 106 can be disposed on the body 102 of the physics package 100 or can be disposed external to the body 102. In an example at least one of the one or more lasers 104, 105, 106 is mounted on a thermal isolation die 114. One or more photodetectors 108 are configured to sense light from within the sensing chamber 103 in order to sense light emitted from atoms in the alkali vapor. The light emitted from the atoms in the alkali vapor can then be used to generate the output for the atomic clock or atomic inertial sensor.

The alkali vapor in the sensing chamber 103 is released from an atomic source 110. The atomic source 110 can be composed of an elemental alkali, a compound of an alkali and another element, an alloy of an alkali and another metal, or a graphite intercalation compound including an alkali. The atomic source 110 is disposed on a thermal isolation die 112 which is mounted such that atoms released form the atomic source 110 enter the sensing chamber 103. That is, the thermal isolation die 112 is disposed in a location that communicates with the sensing chamber 103. FIG. 1 illustrates an example of such a thermal isolation die 112 disposed in a location that communicates with the sensing chamber 103. For example, the thermal isolation die 112 can be mounted within the sensing chamber 103 such that the alkali atoms are released directly into the sensing chamber 103. In another example, the thermal isolation die 112 is mounted in a recess that opens to the sensing chamber as shown in the example of FIG. 1.

Figure 2:
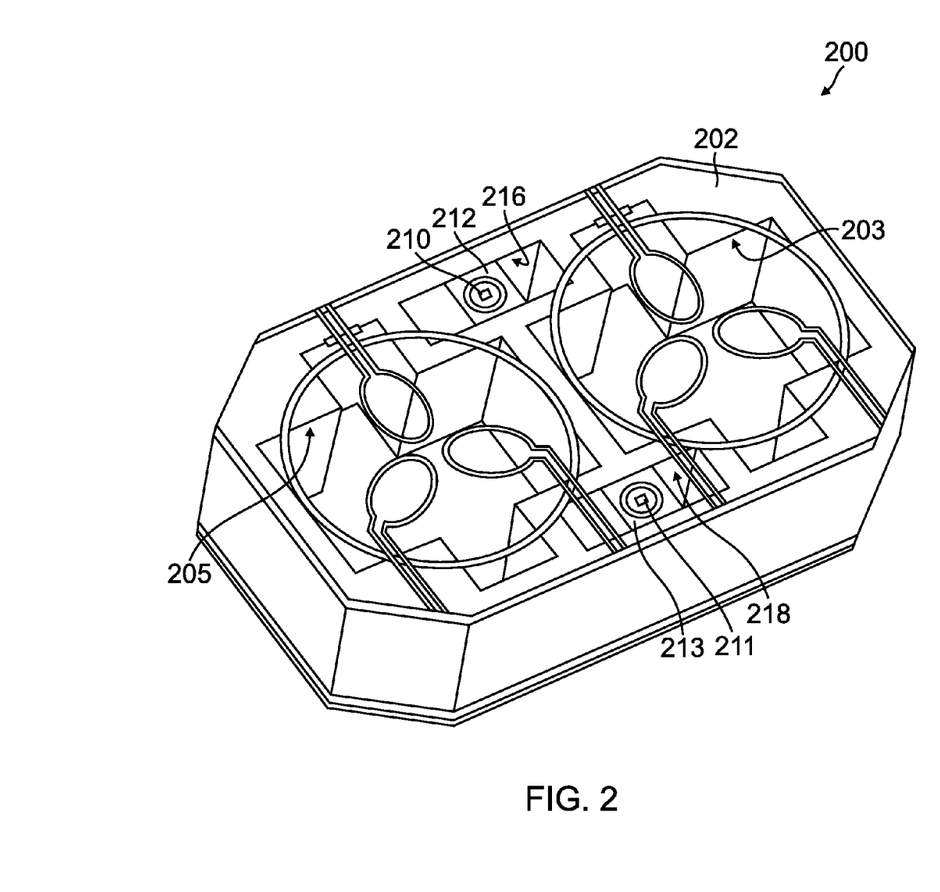
FIG. 2 is a cut-away perspective view of another example physics package for a chip-scale atomic based sensor having an atomic source and heating element disposed on a thermal isolation die.

FIG. 2 illustrates another example of a physics package 200 for a chip-scale atomic based sensor. FIG. 2 illustrates another example of a thermal isolation die 212 having an atomic source 210 that is disposed in a location that communicates with a sensing chamber 203. In physics package 200, the thermal isolation die 212 is mounted in a secondary chamber 216 separate from a sensing chamber 203. Such a secondary chamber 216 communicates with the sensing chamber 203 such that atoms released by the atomic source 210 into the secondary chamber 216 can travel into the sensing chamber 203. A secondary chamber 216 can be used to provide an initial location for atoms released by the atomic source 210 to spread out before traveling into the sensing chamber 203.

Similar to the physics package 100 of FIG. 1, the physics package 200 includes a body 202 defining the sensing chamber 203. The example physics package 200 shown in FIG. 2 corresponds to an inertial sensor and defines two sensing chambers 203, 205. One or more lasers (not shown) and one or more photodetectors (also not shown) are used for each sensing chamber 203, 205 similar to that described above with respect to physics package 100. Additionally, the example physics package 200 of FIG. 2 has two secondary chambers 216, 218 each with an atomic source 210, 211 mounted on a respective thermal isolation die 212, 213.

Figure 3:
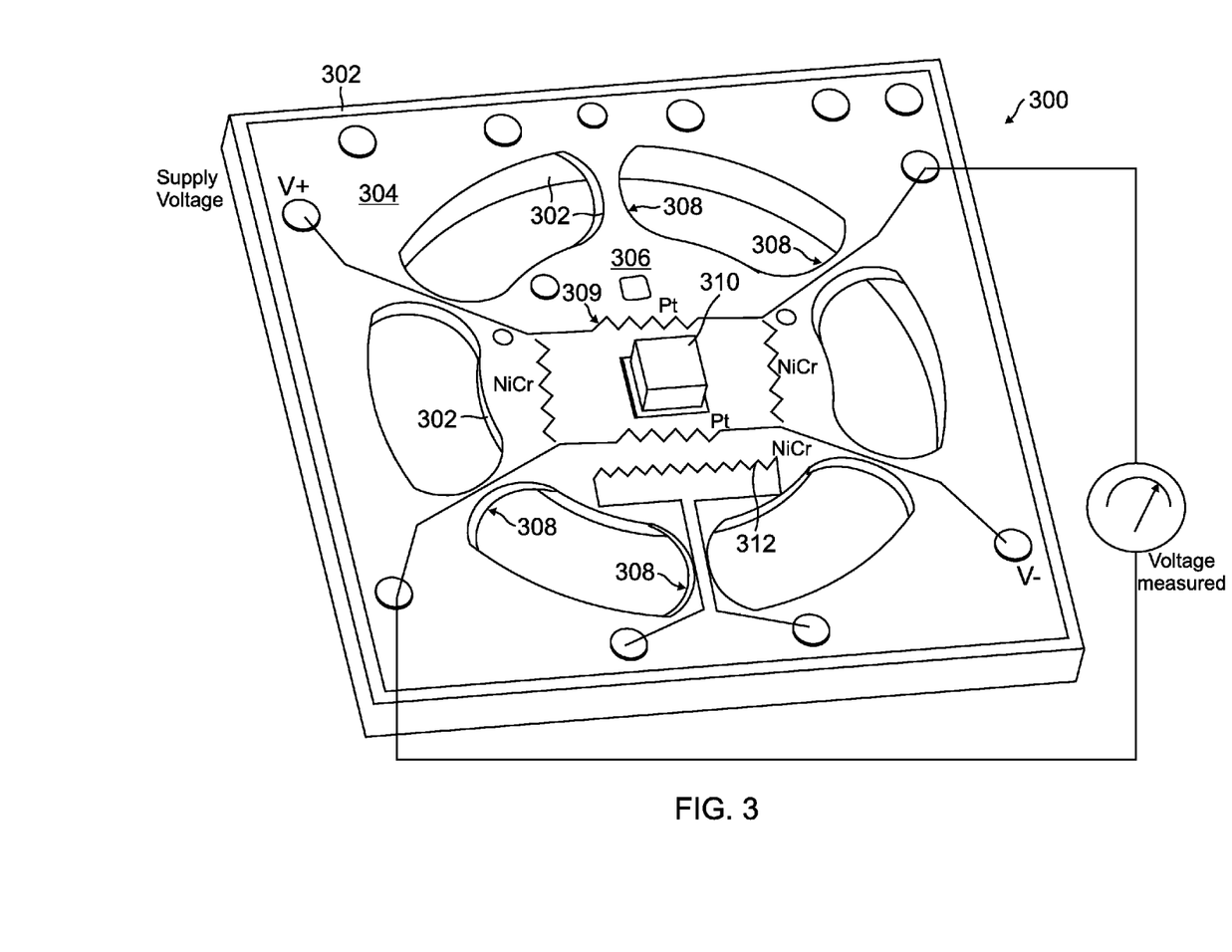
FIG. 3 is a perspective view of an example thermal isolation die for use in the physics package shown in FIGS. 1 and 2, having an atomic source and heating element disposed thereon.

FIG. 3 is a perspective view of an example thermal isolation die 300 that can be used for any of thermal isolation dies 112, 212, 213. The thermal isolation die 300 includes a monolithic substrate 302 that is composed of any suitable material such as silicon. The monolithic substrate 302 defines a frame portion 304, an isolated portion 306 and a plurality of tethers 308 connecting the frame portion 304 to the isolated portion 306. Each of the frame portion 304, the isolated portion 306, and the plurality of tethers 308 is formed by etching the monolithic substrate 302 to remove portions of the substrate 302 leaving the frame portion 304, the isolated portion 306, and the plurality of tethers 308. Accordingly, the plurality of tethers are defined in the substrate 302 (i.e., formed of the material of the substrate 302). The frame portion 304 surrounds the isolated portion 306 which is suspended by the tethers 308. As shown in FIG. 3, much (e.g., at least 75 percent) of the substrate 302 has been removed between the frame portion 304 and the isolated portion 306 such that there are large gaps in the substrate 302 between the isolated portion 306 and the frame 302. This removal of substrate 302 between the frame portion 304 and the isolated portion 306 provides a high thermal isolation for the isolated portion 306 from the frame portion 304. In the example shown in FIG. 3, the isolated portion 306 has a circular shape and an annular gap (except for the tethers 308) surrounds the isolated portion 306 between the isolated portion 306 and the frame 304. The tethers 308 extend through the annular gap from the isolated portion 306 to the frame 304. In other examples, shapes other than circular and annular can be used.

In an example, an insulating layer, such as an oxide layer, is disposed on a top working surface of the substrate 302 to insulate electronic components (e.g., leads) on the top working surface of the substrate 302 from the substrate 302. An atomic source 310 is mounted on the isolated portion 306 of the substrate 302. A heating element 312 is also on the isolated portion 306 of the substrate 302 and is configured to heat the isolated portion 306 and surrounding area. The atomic source 310 can be composed of any appropriate composition such as an elemental alkali, a compound of an alkali and another element, an alloy of an alkali and another metal, or a graphite intercalation compound including an alkali. The composition of the atomic source 310 can be selected to have a vapor pressure that is lower than desired at the highest desired operating temperature for the sensor in which the atomic source 310 is used. Then, the atomic source 310 can be heated by the heating element 312 in a controlled manner to increase and maintain the desired vapor pressure in the sensing chamber. The heating element 312 can be a resistor fabricated into the substrate 302 in the isolated portion 304. In an example, the heating element 312 is a resistor composed of nickel-chromium (NiCr). A plurality of electrical leads extend across one or more of the tethers 308 and couple the heating element 312 to components on or coupled to the frame portion 304.

In operation, the heating element 312 is controlled to control the temperature of the atomic source 310 and maintain a desired vapor pressure in the sensing chamber. In particular, as the temperature of the atomic source 310 increases, the vapor pressure provided by atomic source 310 increases. In a basic example, the heating element 312 is controlled in an open loop manner. Advantageously, disposing the heating element 312 and the atomic source 310 on an isolated portion 306 of a thermal isolation die 300 enables the atomic source 310 be heated with low power. In one example, it takes around 20 mW to heat the atomic source 310 in such an arrangement.

In other examples, the heating element 312 is controlled in a closed loop manner. In one such example, a temperature sensor is disposed on the isolated portion 306 to sense a temperate thereof. A temperature set point is selected based on the desired vapor pressure of the atomic source 310. The temperature sensor senses the temperature of/around the isolated portion 206 and sends a signal indicative thereof to control electronics (not shown). The control electronics are coupled to the heating element 312 and adjust the heat provided by the heating element 312 to maintain the temperature of the isolated portion 306 at the set point. In such an example, the temperature set point can be static. In one implementation of such an example shown in FIG. 3, the temperature sensor is a Wheatstone bridge 309 fabricated into the isolated portion 306 of the substrate 302. Such a Wheatstone bridge 309 can be composed of two nickel-chromium (NiCr) resistors coupled to two platinum (Pt) resistors. A plurality of electrical leads can extend across one or more of the tethers 308 to couple the Wheatstone bridge 309 to other components on or coupled to the frame 304. In an alternative example, the temperature sensor on the isolated portion 306 can be a platinum resistor alone instead of a full Wheatstone bridge.

Figure 4:
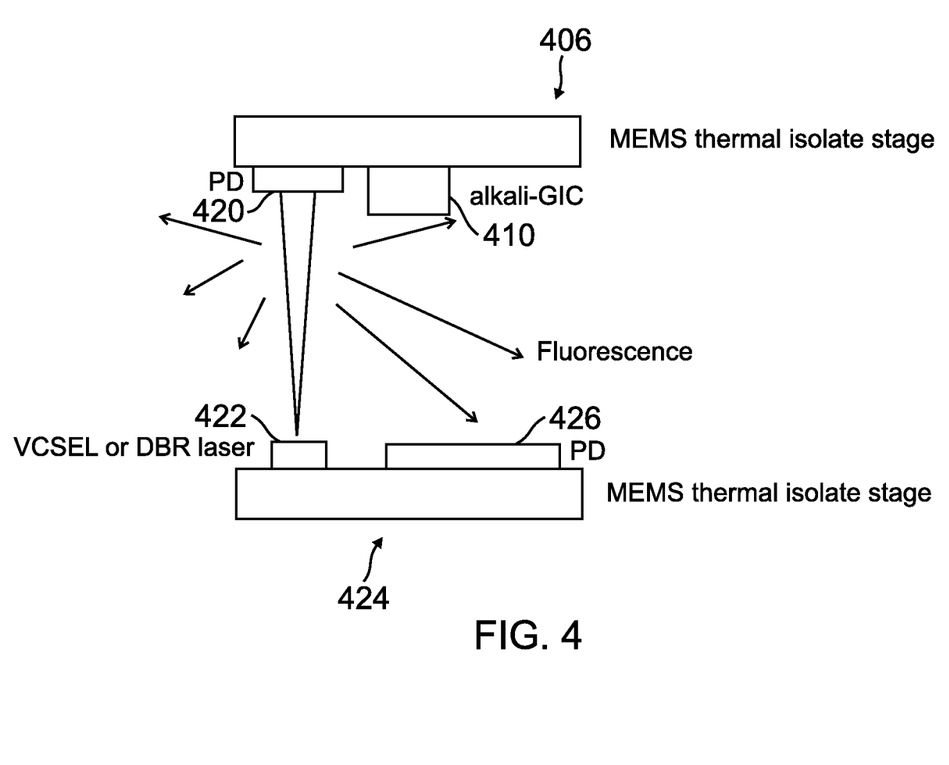
FIG. 4 is a diagram of an example laser and photodetectors for closed loop control of the heating element on the thermal isolation die of FIG. 3 for heating an atomic source.

FIG. 4 is a diagram of another example of closed loop control of the heating element 312. This example illustrates an isolated portion 406 of a thermal isolation die as described above with respect to FIG. 3. The isolated portion 406 has an atomic source 410 mounted thereon. Additionally, a laser 422 is mounted to the body of a chip scale atomic sensor and disposed to emit light into the sensor chamber. In particular, the laser 422 is disposed to emit light into the alkali vapor cloud in the sensing chamber. The laser 422 is locked to the atomic hyperfine transition of the alkali atoms in the alkali vapor (i.e., the alkali atoms released by the atomic source 410). AC modulation can be used the lock the laser to the atomic hyperfine transition as known in the art. A photodetector (e.g., photodetector 420 or 426) is configured to sense light from the sensing chamber based on the light emitted by the laser 422. This light sensed by the photodetector is indicative of the amount of alkali atoms that are present in the alkali vapor cloud. Accordingly, the output from the photodetector is indicative of the vapor pressure of the alkali atoms within the sensing chamber.

The photodetector 420 is a first example of a photodetector that is configured to sense light that is indicative of the amount of alkali atoms in the alkali vapor cloud. The photodetector 420 is disposed to sense the strength of the light from the laser 422 that propagates through the vapor cloud. As the light from the laser 422 propagates through the alkali vapor cloud the light is absorbed by any alkali atoms in its path. Accordingly, the denser the alkali vapor cloud, the less light that is sensed by the photodetector 420. In this first example, the photodetector 420 is aligned with and configured to sense light emitted by a laser 422. The laser 422 and photodetector 420 are disposed such that the light from the laser 422 propagates through the alkali vapor cloud in the sensing chamber.

Photodetector 426 is a second example of a photodetector that is configured to sense light that is indicative of the amount of alkali atoms in the alkali vapor cloud. Photodetector 426 can be used instead of, or in addition to, the photodetector 420. The photodetector 426 is disposed to sense fluorescence emitted by the alkali atoms after the alkali atoms absorb the light from the laser 422. The denser the alkali vapor cloud, the more alkali atoms that are in the path of the light from the laser 422 and, therefore, the more alkali atoms that absorb light from the laser 422. Each alkali atom that absorbs light from the laser 422 emits fluorescence. Therefore, the denser the alkali vapor cloud, the more fluorescence emitted. In this way, a signal from the photodetector 420 indicative of fluorescence sensed can be provided to the control electronics and the heating element 312 can be controlled thereby to maintain a desired vapor pressure in the sensing chamber. Such a photodetector 426 can be mounted in any practical location, including, but not limited to, on the same thermal isolation die (in particular, on the same isolated portion 424) as the laser 422. The isolated portion 424 of the thermal isolation die can have its temperature controlled (e.g., via a heating element similar to that discussed with respect to FIG. 3 above) in order to temperature stabilize the laser 422 and/or second photodetector 426.

In any case, the photodetector(s) 420 and/or 426 outputs a signal indicative the vapor pressure in the sensing chamber to the control electronics coupled to the heating element 312. In an example, the output signal from the photodetector 420, 426 is a DC signal. The control electronics can use this signal to control the heat provided by the heating element 312 based on the density of the alkali vapor cloud in the sensing chamber to maintain a desired vapor pressure within the sensing chamber. A photodetector 420, 426 is also mounted on the isolated portion 406. Advantageously, mounting the photodetector 420, 426 on the same thermal isolation die (in particular, the same isolated portion 406) as the atomic source 410 and heating element provides temperature stabilization for the feedback resistor for the photodetector 420, 426. It is not necessary; however, that the photodetector 420, 426 be mounted on the same thermal isolation die as the atomic source 410 and heating element. Therefore, in other examples, the photodetector 420, 426 is mounted on a different thermal isolation die. In yet other examples, the photodetector 420, 426 is mounted on a structure that is not a thermal isolation die such as the body of the physics package.

The laser 422 can also be mounted on a thermal isolation die (different than the thermal isolation die for the atomic source 410). In particular, the laser 422 can be mounted on an isolated portion 424 of a thermal isolation die that is disposed such that the laser 422 emits light toward the photodetector 420, 426. The laser 422 can be any suitable laser such as a VCSEL or DBR laser.

In some examples, the laser 422 (which is locked to the atomic hyperfine transition) can also be used as a master laser for phase locking other slave lasers used to perform laser cooling and other atomic sensing tasks.

In an example, the temperature of the atomic source 310, 410 can be controlled using both the temperature sensor (e.g., the Wheatstone bridge 309) on the isolated portion 306, 406 in which the atomic source 310, 410 is mounted and the laser 422 and photodetector 420, 426. In particular, the temperature sensor on the isolated portion 306, 406 with the atomic source 310, 410 can be used to provide a coarse adjustment and the laser 422 with the photodetector 420 and/or photodetector 426 can provide a fine adjustment. For example, an initial temperature set point can be selected for the Wheatstone bridge 309 at an initially assumed temperature for the isolated portion 306, 406. The control electronics can control the heating element 312 to maintain the Wheatstone bridge 309 and the initial temperature set point. In an example, the initial temperature set point is around 100 degrees Celsius. While the heating element 312 is being controlled to maintain the Wheatstone bridge 309 at the initial temperature set point, the laser 422 with the photodetector 420, 426 can measure the density of the alkali vapor in the sensing chamber. If the density is lower than desired, the control electronics can increase the temperature set point for the Wheatstone bridge 309 to increase the alkali atoms released by the atomic source 310, 410. If the density is higher than desired, the control electronics can decrease the temperature set point for the Wheatstone bridge 309 and thereby decrease the alkali atoms released by the atomic source 310, 410 and, in some examples, cause the atomic source 310, 410 to re-absorb alkali atoms from the sensing chamber. The control electronics can then maintain the Wheatstone bridge 309 and the adjust temperature set point to fine tune the vapor pressure in the sensing chamber.

The thermal isolation die 300 can be fabricated by forming a doped layer on a portion of a top surface of a substrate 302 with an etch stop such as boron. In particular, at least a portion of the top surface that corresponds to the isolated portion 306, its surrounding gap, and the tethers 308 can be doped. The substrate 302 can then be etched from the backside through the substrate until the doped layer. This etch can etch the area of the backside corresponding to the isolated portion 306, its surrounding gap, and the tethers 308. This etch can be performed, for example, using deep reactive ion etching. After this first etch a layer of the substrate 302 at the top surface remains in the isolated portion 306, its surrounding gap, and the tethers 308. Next, this layer (which comprises a doped layer with, for example, boron) is etched through the front side to form the gaps and thereby to define the tethers 308 and the isolated portion 306. Such a second etch can be performed lithographically. In some examples, the tethers 308 can be formed of materials other than the substrate 302 (e.g., silicon) such as an oxide or nitride of silicon or a suitable glass such as Pyrex.

An oxide layer can be formed on the top surface of the frame 304, isolated portion 306, and tethers 308 to insulate the substrate 302 from the electrical components (e.g., leads). Electrical leads, the heating element 312, Wheatstone bridge 309 and other any other components can be fabricated (patterned) in the top surface. The heating element 312 and the Wheatstone bridge 309 can be fabricated in the isolated portion 306 and the electrical leads can be fabricated across one or more tethers 308 to couple components on the isolated portion 306 to components on or coupled to the frame portion 304. For example, the NiCr heating element 312 can be a lithographically patterned resistor in the isolated portion 306. One or more vias can be fabricated through the frame portion 304 from the frontside to the backside of the substrate to couple the electrical leads on the frontside to components coupled to the backside of the frame portion 304. The atomic source 310 can be mounted on the isolated portion 306. The backside of the frame portion 304 can be mounted to another member for attaching the thermal isolation die 300 to another structure.

EXAMPLE EMBODIMENTS

Example 1 includes a chip scale atomic sensor comprising: a body that defines at least one sensing chamber; a thermal isolation die mounted to the body, the thermal isolation die disposed in a location that communicates with the at least one sensing chamber, the thermal isolation die including: a substrate defining a frame portion and an isolated portion; a plurality of tethers mechanically coupling the isolated portion of the substrate to the frame portion; an atomic source mounted on the isolated portion of the substrate; and a heating element on the isolated portion and configured to heat the atomic source.

Example 2 includes the chip scale atomic sensor of Example 1, wherein the thermal isolation die includes a temperature sensor disposed on the isolated portion, the temperature sensor configured to sense a temperature proximate the atomic source, wherein the chip scale atomic sensor includes control electronics configured to obtain temperature readings from the temperature sensor and control the heating element to maintain the temperature proximate the atomic source at a temperature set point.

Example 3 includes the chip scale atomic sensor of Example 2, wherein the temperature sensor is a Wheatstone bridge.

Example 4 includes the chip scale atomic sensor of any of Examples 2-3, wherein the thermal isolation die includes a plurality of electrical leads disposed in part on the plurality of tethers, the plurality of electrical leads electrically coupled to the heater and the temperature sensor.

Example 5 includes the chip scale atomic sensor of any of Examples 2-4, comprising: a laser disposed to emit light into the sensing chamber, wherein the laser is locked to an atomic hyperfine transition of alkali atoms of the atomic source; and a photodetector disposed to sense light in the sensing chamber indicative of the vapor pressure in the sensing chamber, wherein the control electronics are configured to receive a signal from the photodetector and to control the heating element based thereon to maintain a desired vapor pressure of alkali atoms within the sensing chamber.

Example 6 includes the chip scale atomic sensor of Example 5, wherein the photodetector is aligned with and configured to sense light emitted by the laser after the light passes through a vapor cloud of alkali atoms in the sensing chamber.

Example 7 includes the chip scale atomic sensor of any of Examples 5-6, wherein the photodetector is disposed to sense fluorescence emitted by alkali atoms in a vapor cloud in the sensing chamber after the alkali atoms absorb light from the laser.

Example 8 includes the chip scale atomic sensor of any of Examples 5-7, wherein the photodetector is mounted on the isolated portion of the thermal isolation die.

Example 9 includes the chip scale atomic sensor of Example 8, wherein the laser is mounted on an isolated portion of a second thermal isolation die.

Example 10 includes the chip scale atomic sensor of any of Examples 5-9, wherein the control electronics are configured to adjust the temperature set point based on the signal indicative of vapor pressure from the photodetector to maintain a vapor pressure in the sensing chamber.

Example 11 includes the chip scale atomic sensor of any of Examples 1-10, wherein the plurality of tethers are defined in the substrate.

Example 12 includes the chip scale atomic sensor of any of Examples 1-11, wherein the substrate is composed of silicon.

Example 13 includes the chip scale atomic sensor of any of Examples 1-12, wherein the atomic source includes one of a compound of an alkali and another element, an alloy of an alkali and another metal, or a graphite intercalation compound including an alkali.

Example 14 includes the chip scale atomic sensor of any of Examples 1-13, wherein the thermal isolation die is disposed within the sensing chamber, in a recess that opens to the sensing chamber, or in a secondary chamber that communicates with the sensing chamber.

Example 15 includes a method of controlling a vapor pressure in a chip scale atomic sensor, the method comprising: sensing a temperature proximate an atomic source; controlling a heating element proximate the atomic source based on the sensed temperature to maintain the temperature proximate the atomic source at a temperature set point; emitting light from a laser toward a vapor cloud of alkali atoms in a sensing chamber of the chip scale atomic sensor; sensing light in the sensing chamber, the light indicative of a vapor pressure of alkali atoms in the sensing chamber; and adjusting the temperature set point based on the sensed light in the sensing chamber to maintain the vapor pressure in the sensing chamber at a desired level.

Example 16 includes the method of Example 15, wherein sensing light includes one or more of sensing light emitted by the laser that passed through the vapor cloud and sensing fluorescence emitted by the alkali atoms after the alkali atoms absorb light from the laser.

Example 17 includes a chip scale atomic sensor comprising: a body that defines a sensing chamber; a thermal isolation die mounted to the body, the thermal isolation die disposed in a location that communicates with the sensing chamber, the thermal isolation die including: a substrate composed of silicon, the substrate defining a frame portion, an isolated portion, and a plurality of tethers mechanically extending between the isolated portion and the frame portion, wherein plurality of tethers extend through a gap in the substrate between the frame portion and the isolated portion; an atomic source mounted on the isolated portion of the substrate; a heating element mounted on the isolated portion of the substrate; and a plurality of electrical leads disposed in part on the plurality of tethers, the plurality of leads electrically coupled to the heater.

Example 18 includes the chip scale atomic sensor of Example 17, comprising: a laser disposed to emit light into the sensing chamber, wherein the laser is locked to an atomic hyperfine transition of alkali atoms of the atomic source; and a photodetector disposed to sense light in the sensing chamber indicative of the vapor pressure in the sensing chamber, wherein the control electronics are configured to receive a signal from the photodetector and to control the heating element based thereon to maintain a desired vapor pressure of alkali atoms within the sensing chamber.

Example 19 includes the chip scale atomic sensor of Example 18, wherein the thermal isolation die includes a temperature sensor disposed on the isolated portion, the temperature sensor configured to sense a temperature proximate the atomic source, wherein the chip scale atomic sensor includes control electronics configured to obtain temperature readings from the temperature sensor and control the heating element to maintain the temperature proximate the atomic source at a temperature set point.

Example 20 includes the chip scale atomic sensor of Example 19, wherein the control electronics are configured to adjust the temperature set point based on the signal indicative of vapor pressure from the photodetector to maintain a vapor pressure in the sensing chamber.

What is claimed is:

1. A chip scale atomic sensor comprising:
a body that defines at least one sensing chamber;
a thermal isolation die mounted to the body, the thermal isolation die disposed in a location that communicates with the inside of at least one sensing chamber, the thermal isolation die including:
  a substrate defining a frame portion and an isolated portion;
  a plurality of tethers mechanically coupling the isolated portion of the substrate to the frame portion;
  an atomic source mounted on the isolated portion of the substrate; and
  a heating element on the isolated portion and configured to heat the atomic source.

2. The chip scale atomic sensor of claim 1, wherein the thermal isolation die includes a temperature sensor disposed on the isolated portion, the temperature sensor configured to sense a temperature proximate the atomic source,
wherein the chip scale atomic sensor includes control electronics configured to obtain temperature readings from the temperature sensor and control the heating element to maintain the temperature proximate the atomic source at a temperature set point.

3. The chip scale atomic sensor of claim 2, wherein the temperature sensor is a Wheatstone bridge.

4. The chip scale atomic sensor of claim 2, wherein the thermal isolation die includes a plurality of electrical leads disposed in part on the plurality of tethers, the plurality of electrical leads electrically coupled to the heating element and the temperature sensor.

5. The chip scale atomic sensor of claim 2, comprising:
a laser disposed to emit light into the sensing chamber, wherein the laser is locked to an atomic hyperfine transition of alkali atoms of the atomic source; and
a photodetector disposed to sense light in the sensing chamber indicative of the vapor pressure in the sensing chamber,
wherein the control electronics are configured to receive a signal from the photodetector and to control the heating element based thereon to maintain a desired vapor pressure of alkali atoms within the sensing chamber.

6. The chip scale atomic sensor of claim 5, wherein the photodetector is aligned with and configured to sense light emitted by the laser after the light passes through a vapor cloud of alkali atoms in the sensing chamber.

7. The chip scale atomic sensor of claim 5, wherein the photodetector is disposed to sense fluorescence emitted by alkali atoms in a vapor cloud in the sensing chamber after the alkali atoms absorb light from the laser.

8. The chip scale atomic sensor of claim 5, wherein the photodetector is mounted on the isolated portion of the thermal isolation die.

9. The chip scale atomic sensor of claim 8, wherein the laser is mounted on an isolated portion of a second thermal isolation die.

10. The chip scale atomic sensor of claim 5, wherein the control electronics are configured to adjust the temperature set point based on the signal indicative of vapor pressure from the photodetector to maintain a vapor pressure in the sensing chamber.

11. The chip scale atomic sensor of claim 1, wherein the plurality of tethers are defined in the substrate.

12. The chip scale atomic sensor of claim 1, wherein the substrate is composed of silicon.

13. The chip scale atomic sensor of claim 1, wherein the atomic source includes one of a compound of an alkali and another element, an alloy of an alkali and another metal, or a graphite intercalation compound including an alkali.

14. The chip scale atomic sensor of claim 1, wherein the thermal isolation die is disposed within the sensing chamber, in a recess that opens to the sensing chamber, or in a secondary chamber that communicates with the sensing chamber.

15. A method of controlling a vapor pressure in a chip scale atomic sensor, the method comprising:
sensing a temperature proximate an atomic source;
controlling a heating element proximate the atomic source based on the sensed temperature to maintain the temperature proximate the atomic source at a temperature set point;
emitting light from a laser toward a vapor cloud of alkali atoms in a sensing chamber of the chip scale atomic sensor;
sensing light in the sensing chamber, the light indicative of a vapor pressure of alkali atoms in the sensing chamber; and
adjusting the temperature set point based on the sensed light in the sensing chamber to maintain the vapor pressure in the sensing chamber at a desired level.

16. The method of claim 15, wherein sensing light includes one or more of sensing light emitted by the laser that passed through the vapor cloud and sensing fluorescence emitted by the alkali atoms after the alkali atoms absorb light from the laser.

17. A chip scale atomic sensor comprising:
a body that defines a sensing chamber;
a thermal isolation die mounted to the body, the thermal isolation die disposed in a location that communicates with the sensing chamber, the thermal isolation die including:
   a substrate composed of silicon, the substrate defining a frame portion, an isolated portion, and a plurality of tethers mechanically extending between the isolated portion and the frame portion, wherein plurality of tethers extend through a gap in the substrate between the frame portion and the isolated portion;
   an atomic source mounted on the isolated portion of the substrate;
   a heating element on the isolated portion of the substrate; and
   a plurality of electrical leads disposed in part on the plurality of tethers, the plurality of leads electrically coupled to the heating element.

18. The chip scale atomic sensor of claim 17, comprising:
a laser disposed to emit light into the sensing chamber, wherein the laser is locked to an atomic hyperfine transition of alkali atoms of the atomic source; and
a photodetector disposed to sense light in the sensing chamber indicative of the vapor pressure in the sensing chamber,
wherein the control electronics are configured to receive a signal from the photodetector and to control the heating element based thereon to maintain a desired vapor pressure of alkali atoms within the sensing chamber.

19. The chip scale atomic sensor of claim 18, wherein the thermal isolation die includes a temperature sensor disposed on the isolated portion, the temperature sensor configured to sense a temperature proximate the atomic source,
wherein the chip scale atomic sensor includes control electronics configured to obtain temperature readings from the temperature sensor and control the heating element to maintain the temperature proximate the atomic source at a temperature set point.

20. The chip scale atomic sensor of claim 19, wherein the control electronics are configured to adjust the temperature set point based on the signal indicative of vapor pressure from the photodetector to maintain a vapor pressure in the sensing chamber.

21. A thermal isolation die comprising:
a substrate defining a frame portion and an isolated portion;
a plurality of tethers mechanically coupling the isolated portion of the substrate to the frame portion;
an atomic source mounted directly on the isolated portion of the substrate; and
a heating element mounted on the isolated portion and configured to heat the atomic source.

22. The thermal isolation die of claim 21, further comprising a temperature sensor disposed on the isolated portion, the temperature sensor configured to sense a temperature proximate the atomic source.

23. The thermal isolation die of claim 22, wherein the temperature sensor is a Wheatstone bridge.

24. The thermal isolation die of claim 22, wherein the thermal isolation die includes a plurality of electrical leads disposed, in part, on the plurality of tethers, the plurality of electrical leads electrically coupled to the heating element and the temperature sensor.

25. The thermal isolation die of claim 21, wherein the atomic source includes one of a compound of an alkali and another element, an alloy of an alkali and another metal, or a graphite intercalation compound including an alkali.

26. The chip scale atomic sensor of claim 1, wherein the atomic source comprises a graphite intercalation compound including an alkali.

27. The chip scale atomic sensor of claim 17, wherein the atomic source comprises a graphite intercalation compound including an alkali.

* * * * *